(12) United States Patent
Weber et al.

(10) Patent No.: US 8,004,682 B2
(45) Date of Patent: Aug. 23, 2011

(54) METHODS AND SYSTEMS FOR ANALYZING A VOLUME OF GAS

(75) Inventors: Werner Weber, München (DE); Rudolf Lachner, Ingolstadt (DE)

(73) Assignee: Infineon Technologies AG, Neubiberg (DE)

( * ) Notice: Subject to any disclaimer, the term of this patent is extended or adjusted under 35 U.S.C. 154(b) by 689 days.

(21) Appl. No.: 12/104,125

(22) Filed: Apr. 16, 2008

(65) Prior Publication Data

US 2009/0260417 A1    Oct. 22, 2009

(51) Int. Cl.
G01N 21/00 (2006.01)
G01N 27/00 (2006.01)
G01J 1/42 (2006.01)

(52) U.S. Cl. .......... 356/432; 356/437; 73/23.2; 250/393

(58) Field of Classification Search .......... 356/432–439, 356/4.01, 5.01; 250/393, 343, 339.05, 339.01; 324/637, 316, 639, 6, 58.5 B
See application file for complete search history.

(56) References Cited

U.S. PATENT DOCUMENTS

| | | | | |
|---|---|---|---|---|
| 3,788,742 A * | 1/1974 | Garbuny | .................. | 356/5.03 |
| 3,873,942 A * | 3/1975 | Reilly | .................. | 372/95 |
| 4,132,943 A * | 1/1979 | Gournay et al. | .................. | 324/335 |
| 4,160,373 A | 7/1979 | Fastaia et al. | | |
| 5,483,546 A * | 1/1996 | Johnson et al. | .................. | 372/10 |
| 6,084,415 A * | 7/2000 | B.ang..ang.th | .................. | 324/639 |
| 6,335,625 B1 * | 1/2002 | Bryant et al. | .................. | 324/637 |
| 6,384,903 B1 * | 5/2002 | Fuller | .................. | 356/4.01 |
| 6,841,778 B1 * | 1/2005 | Shifflett et al. | .......... | 250/339.05 |
| 6,943,884 B2 * | 9/2005 | Rice | .................. | 356/437 |
| 6,983,639 B1 | 1/2006 | DiDomenico et al. | | |
| 7,012,696 B2 | 3/2006 | Orr et al. | | |
| 2004/0227088 A1 | 11/2004 | Trotz et al. | | |
| 2007/0081157 A1 | 4/2007 | Csutak et al. | | |
| 2007/0145276 A1 | 6/2007 | Zhang et al. | | |

FOREIGN PATENT DOCUMENTS

| | | |
|---|---|---|
| DE | 3829157 A1 * | 3/1990 |
| WO | 2007135382 A2 | 11/2007 |

OTHER PUBLICATIONS

"Far-infrared terahertz time-domain spectroscopy of flames", R.A. Cheville and D. Grischkowsky, Optics Letters, vol. 20, No. 15, Aug. 1, 1995, 2 pgs.

"T-ray Tomography", Daniel M. Mittleman, Stefan Hunsche, Luc Boivin and Martin C. Nuss, Optics Letters, vol. 22, No. 12, Jun. 15, 1997, 2 pgs.

"Catalytic Diesel After-treatment Control: Current Challenges", Guido Saracco, Torino SAE OPD_Optimizing_Powertrain, Published Dec. 9, 2007, 13 pgs.

"High Frequency and Quantum Electronics", P. Haring Bolivar, University of Siegen, Feb. 7, 2007, 58 pgs.

* cited by examiner

*Primary Examiner* — Sang Nguyen

(74) *Attorney, Agent, or Firm* — Eschweiler & Associates, LLC (57) ABSTRACT

One embodiment relates to a method for determining a concentration of a molecular species of interest. In this method, electromagnetic radiation is transmitted into a volume of gas within an output exhaust system. The transmitted electromagnetic radiation has a first intensity at a characteristic frequency that is associated with a transition of the molecular species of interest. Electromagnetic radiation is then received from the volume of gas at a second intensity. The method then correlates the first intensity to the second intensity to determine the concentration of the molecular species of interest within the volume of gas. Other methods and systems are also disclosed.

19 Claims, 6 Drawing Sheets

METHODS AND SYSTEMS FOR ANALYZING A VOLUME OF GAS

FIELD OF INVENTION

The present invention relates generally to methods and systems for analyzing a molecular species of interest within a volume of gas.

BACKGROUND OF THE INVENTION

Environmental issues are becoming more and more important for businesses today. Consumers are requesting products that are more environmentally friendly, and businesses are responding to their requests.

Due to the increased awareness of global warming, air pollution is becoming a particularly important environmental issue. As such, companies are trying to provide products that reduce air pollution. One way of reducing air pollution is by reducing harmful exhaust from vehicles, manufacturing facilities, and the like.

SUMMARY OF THE INVENTION

The following presents a simplified summary in order to provide a basic understanding of one or more aspects of the invention. This summary is not an extensive overview of the invention, and is neither intended to identify key or critical elements of the invention, nor to delineate the scope thereof. Rather, the primary purpose of the summary is to present some concepts of the invention in a simplified form as a prelude to the more detailed description that is presented later.

One embodiment relates to a method for determining a concentration of a molecular species of interest. In this method, electromagnetic radiation is transmitted into a volume of gas within an output exhaust system. The transmitted electromagnetic radiation has a first intensity at a characteristic frequency that is associated with a transition of the molecular species of interest. Electromagnetic radiation is then received from the volume of gas at a second intensity. The method then correlates the first intensity to the second intensity to determine the concentration of the molecular species of interest within the volume of gas. Other methods and systems are also disclosed.

The following description and annexed drawings set forth in detail certain illustrative aspects and implementations of the invention. These are indicative of only a few of the various ways in which the principles of the invention may be employed.

DETAILED DESCRIPTION OF THE INVENTION

One or more implementations of the present invention will now be described with reference to the attached drawings, wherein like reference numerals are used to refer to like elements throughout. Although embodiments are described further below in the context of gaseous monitoring systems for vehicles (e.g., cars, trucks, motorcycles, planes, trains, etc.), aspects of the invention are also applicable to gaseous monitoring systems for factories, businesses, scientific instruments, and the like.

One way to reduce pollutants in vehicle exhaust is to monitor and control the combustion process in a vehicle's engine. Accordingly, some embodiments discussed herein relate to low-cost gaseous monitoring systems that are sufficiently robust to be mounted in a vehicle for day-to-day gaseous monitoring, such as exhaust monitoring. In some embodiments, this may be achieved with a frequency-tunable transmitter and frequency-tunable receiver that cooperatively detect a concentration of a molecular species of interest within a volume of gas. In one embodiment, the molecular species of interest could be selected from the group: nitrous oxide ($NO_x$), ammonia, CO, $CO_2$, $H_2O$, $O_2$, $O_3$, hydrocarbons, and combinations thereof. In some embodiments, the molecular species of interest will have molecular transitions (e.g., rotational, vibrational or other transitions) that fall within a range of frequencies (energies) ranging from about 1 GHz to about 10 THz. In one embodiment, the transmitter and receiver make use of silicon based technologies that facilitate gaseous monitoring in this frequency range.

The gaseous monitoring systems discussed herein take advantage of the fact that every molecular species has its own unique set of discrete energy levels, which are somewhat akin to a "fingerprint" for the molecular species. By measuring how a mixture of different molecular species interacts with photons of various frequencies or energies ($E=h\nu$ or equivalently $E=h\lambda/c$), a gaseous monitoring system generates a frequency spectrum that is indicative of what molecular species are present in the mixture. By comparing the measured frequency spectrum with known characteristic frequencies for different molecular species, the system can determine concentrations for respective molecular species within the mixture.

Figure 1:
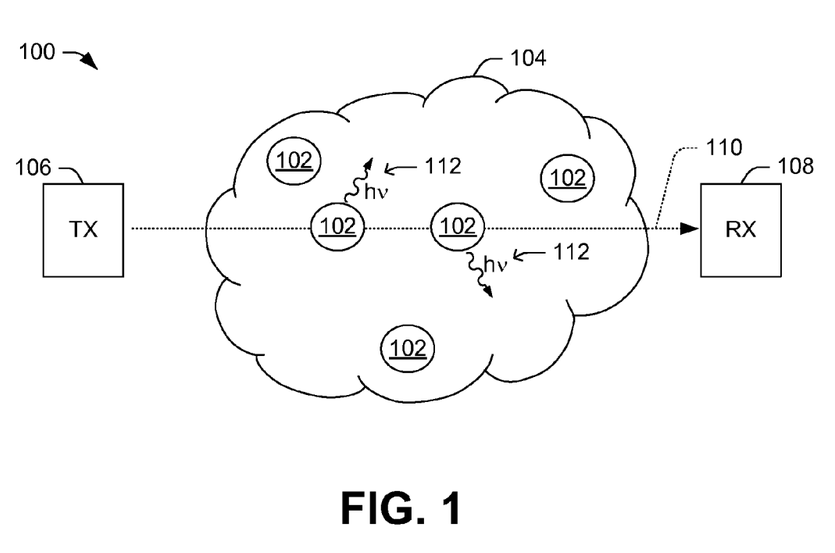
FIG. 1 shows a gaseous monitoring system that takes an absorption measurement in accordance with an embodiment of the present invention.

FIG. 1 depicts a gaseous monitoring system 100 for detecting a concentration of a molecular species of interest 102 within a volume of gas 104. This monitoring system 100 is arranged to measure the extent that the molecular species of interest 102 absorbs radiation, while other embodiments (e.g., FIG. 3) are arranged to measure the extent that an excited state of the molecular species of interest emits radiation.

To facilitate the desired functionality, the gaseous monitoring system 100 includes a transmitter 106 and a receiver 108, which are separated from one another by the volume of gas 104. To detect the concentration of the molecular species of interest 102, the transmitter 106 transmits electromagnetic radiation (photons) through the volume of gas 104 along a transmission path 110. Depending on the implementation, the electromagnetic radiation could be transmitted uni-directionally along the transmission path 110 or multi-directionally (e.g., all directions from the transmitter including along the transmission path). In any event, the radiation is transmitted with a transmitted intensity at a characteristic frequency associated with the molecular species of interest 102.

If a molecule of the molecular species of interest 102 is present along the transmission path 110, the molecule 102 may absorb a photon at the characteristic frequency. This causes the molecule 102 to be briefly excited to a higher energy state. After this brief excitation, the molecule 102 relaxes to a lower energy state, typically by emitting a photon 112 in a random direction. In some instances, the emitted photons 112 will have the same energy as a photon in the transmitted radiation, but in other instances the emitted photon 112 will have a different energy from a photon in the transmitted beam.

The receiver 108 then receives whatever radiation passes through the volume of gas 104, and measures a received intensity of the electromagnetic radiation at the characteristic frequency. If a molecule 102 absorbed a photon at the characteristic frequency (and emitted a photon in another direction), the received intensity will be less than the transmitted intensity. On the other hand, if molecules 102 are not present, the received radiation may be approximately equal to the transmitted radiation.

Figure 2:
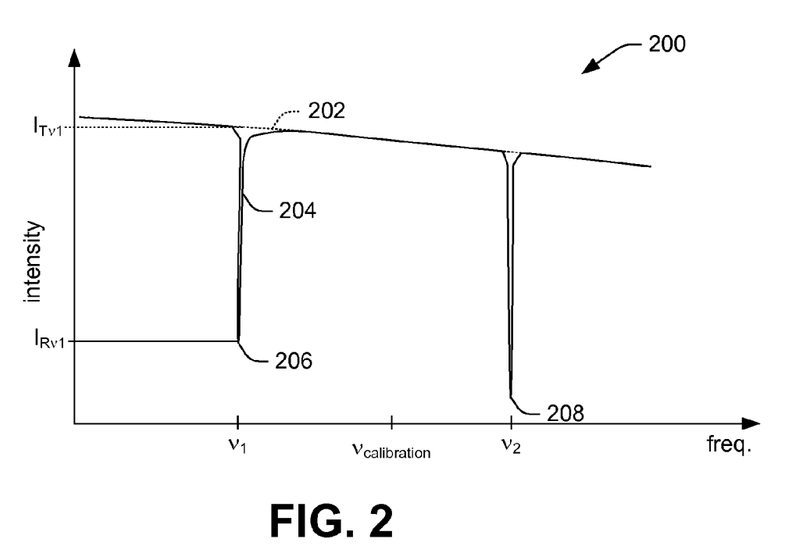
FIG. 2 shows a spectrum consistent with an absorption measurement in accordance with the system of FIG. 1.

FIG. 2 depicts an absorption spectrum 200 that includes both the transmitted radiation 202 and received radiation 204. Two "dips" 206, 208 at characteristic frequencies $v1$, $v2$, respectively correspond to energies $hv1$, $hv2$ at which transmitted photons were absorbed by the molecular species of interest. The "dips" 206, 208 will tend to become "deeper" as the concentration of the molecular species of interest increases, because in higher concentrations it will be more likely that the photons interact with the molecular species of interest and are absorbed. Therefore, in one embodiment, the gaseous monitoring system 100 can compare the transmitted intensity (e.g., $I_{Tv1}$) with the received intensity (e.g., $I_{Rv1}$) to determine the concentration. By scanning from one characteristic frequency (e.g., $v1$) to another characteristic frequency (e.g., $v2$), the transmitter 106 and receiver 108 can accurately determine a spectrum associated with the volume of gas 104. Based on the spectrum, the monitoring system 100 can determine concentrations for one or more molecular species that are present in the volume of gas 104.

In another embodiment, the monitoring system 100 compares the received intensity at the characteristic frequency (e.g., $I_{Rv1}$) to a received intensity at non-characteristic frequency $v_{calibration}$. Because $I_{Rv1}$ depends strongly on the absorption of the molecular species of interest but $I_{Rv\_calibration}$ does not, $I_{Rv1}/I_{Rv\_calibration}$ is also a measure of the concentration of molecular species of interest.

Figure 3:
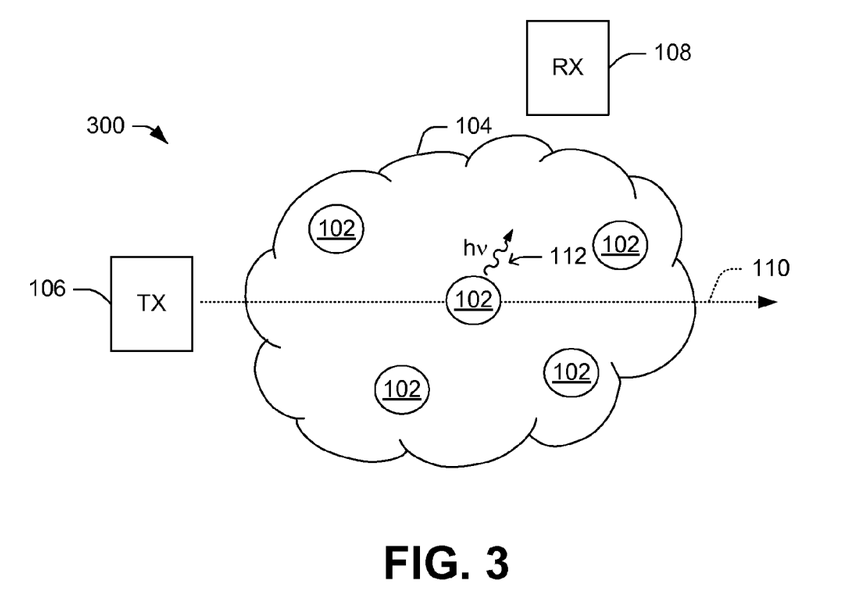
FIG. 3 shows a gaseous monitoring system that takes an emission measurement in accordance with an embodiment of the present invention.

Referring now to FIG. 3, another embodiment of a gaseous monitoring system 300 is depicted. Much like the previous embodiment, the system 300 includes a transmitter 106 and a receiver 108, which are separated from one another by a volume of gas 104. However, in this embodiment the receiver 108 is positioned off of the transmission path 110 (i.e., is not aligned with the transmission path). In this way, the gaseous monitoring system 300 measures emitted photons 112 (instead of measuring absorbed photons as in FIG. 1-2).

To detect whether the molecular species of interest 102 is present in the volume of gas 104, the transmitter 106 transmits electromagnetic radiation through the volume of gas 104 along the transmission path 110. Molecules of the molecular species 102 absorb photons and then emit photons 112, where some emitted photons are detected by the receiver 108. Accordingly, the receiver 108 may measure a received intensity at a characteristic frequency that corresponds to emitted photons. Because the emitted photons are typically emitted in a random direction, the receiver 108 may at least partially surround the volume of gas 104 in some embodiments to increase the likelihood of detecting emitted photons 112.

Figure 4:
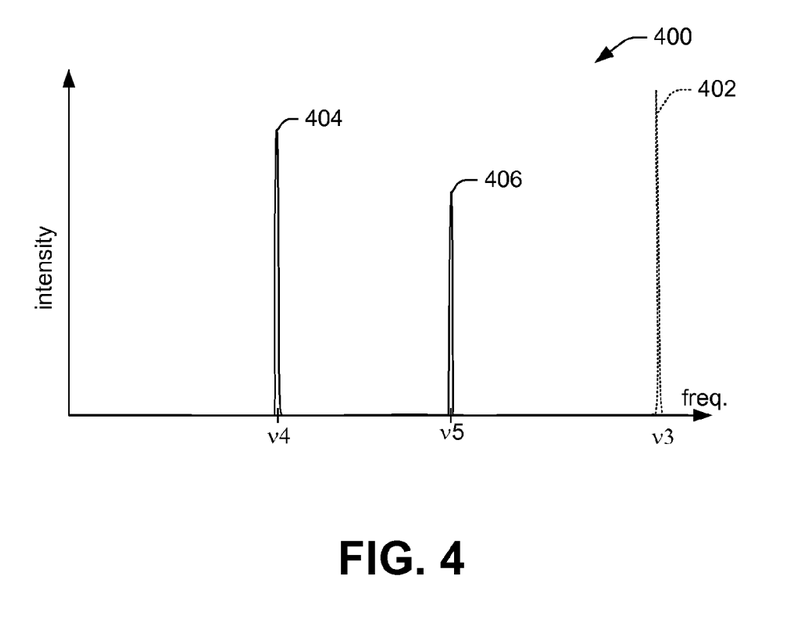
FIG. 4 shows a spectrum consistent with an emission measurement in accordance with the system of FIG. 3.

FIG. 4 shows one example of an emission spectrum 400 that includes both the transmitted radiation 402 and the received radiation. As shown, the transmitted radiation 402 is transmitted at a characteristic frequency $v3$ at which a molecular species of interest absorbs energy to enter an excited state. To relax back down from the excited state to a lower energetic state, the excited molecule will emit a photon that corresponds to another characteristic frequency. In FIG. 4's example, two peaks 404, 406 at characteristic frequencies $v4$, $v5$, respectively, correspond to energies $hv4$, $hv5$, respectively, at which photons were emitted by the molecular species of interest. The peaks will tend to become "higher" as the concentration of the molecular species of interest increases, because in higher concentrations it will be more likely that the photons will collide with the molecular species of interest, causing more emissions.

In some embodiments, the transmitter 106 and receiver 108 can be adapted to operate within a vehicle's combustion engine or output exhaust system. In one embodiment, for example, a gaseous monitoring system 100 or 300 is placed between the engine and the catalytic converter. Due to the harsh environment (e.g., high temperature, corrosive chemistries), previous systems are believed to be unable to achieve adequate reliabilities in these vehicle locations. To facilitate the improved reliability, in some embodiments the transmitter 106 and receiver 108 may be implemented in semiconductor circuits, such as silicon circuits. In addition to improved reliability, silicon circuits are also advantageous in that they are relatively inexpensive to produce. This allows gaseous monitoring systems 100 or 300 to be produced and deployed on a vehicle-by-vehicle basis in a cost-effective manner.

Figure 5:
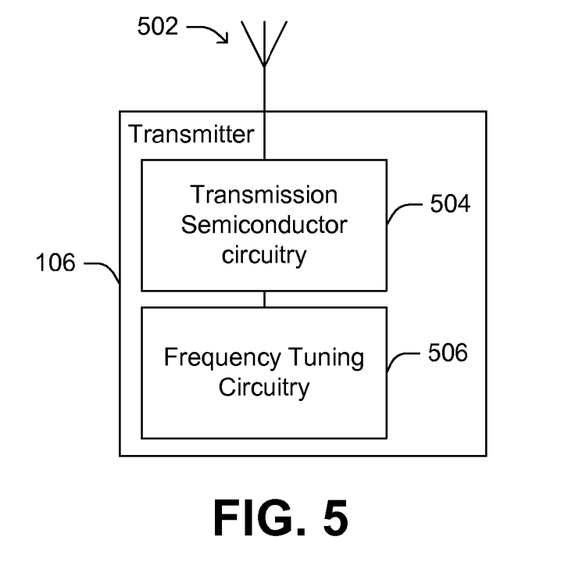
FIG. 5 shows a more detailed embodiment of a transmitter in accordance with an embodiment of the present invention.
Figure 6:
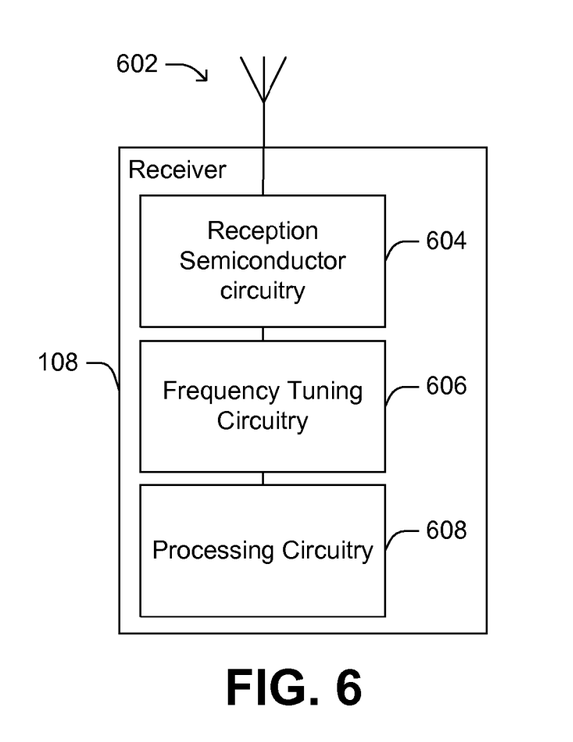
FIG. 6 shows a more detailed embodiment of a receiver in accordance with an embodiment of the present invention.

FIGS. 5-6 depict embodiments of a transmitter 106 and receiver 108, respectively, which can include silicon circuits. More particularly, FIG. 5 shows a frequency-tunable transmitter 106 that includes a transmit antenna 502, transmission semiconductor circuitry 504, and frequency tuning circuitry 506.

In some embodiments, the transmit antenna 502 is suitable for unidirectional transmission, but in other embodiments the transmit antenna 502 is suitable for multi-direction transmission. For example, in one embodiment, a unidirectional transmit antenna comprises a patch antenna.

The transmission semiconductor circuitry 504 includes a semiconductor circuit for providing a time-varying voltage on the transmit antenna 502. The transmission semiconductor circuitry 504 could include a power amplifier, low-noise amplifier, voltage controlled oscillator or other circuit for providing the time-varying voltage. In some embodiments, the transmission semiconductor circuitry 504 may include a bipolar junction transistor (BJT) or metal oxide semiconductor transistor (MOSFET) coupled to the transmit antenna 502, either of which is capable of operating from approximately one gigahertz up to several terahertz.

The frequency tuning circuitry 506 adjusts the frequency at which the transmission semiconductor circuitry 504 provides the time-varying voltage. Thus, the frequency tuning circuitry 506 can adjust the frequency to "scan" through a relatively wide bandwidth over time.

FIG. 6 depicts a frequency-tunable receiver 108 that includes a receive antenna 602, reception semiconductor circuitry 604, frequency tuning circuitry 606, and processing circuitry 608. Like the transmit antenna, the receive antenna 602 comprises a patch antenna in one embodiment. The receive antenna receives photons which are converted into a time-varying voltage.

The reception semiconductor circuitry 604 may include a power amplifier, low-noise amplifier, voltage controlled oscillator or other circuit for amplifying the received time-varying voltage. In some embodiments, the reception semiconductor circuitry 604 may include a bipolar junction transistor (BJT) or metal oxide semiconductor transistor (MOSFET) coupled to the receive antenna 602, either of which is capable of operating from approximately one gigahertz up to several terahertz.

In one embodiment, the frequency tuning circuitry 606 in the receiver 108 is synchronized to that of the transmitter 106. Typically, the frequency tuning circuits 506, 606 stay synchronized with one another by using positive feedback based on the data stream transmitted between the transmitter 106 and receiver 108. In other embodiments, however, the frequency tuning circuits 506, 606 are tuned independent of one another. For example, the receiver 108 could continuously receive at one frequency while the transmitter 106 scans over a range of frequencies.

The processing circuitry 608 is adapted to analyze the electromagnetic radiation received from the transmitter 106. For example, the processing circuitry 608 may include a microprocessor, digital signal processor (DSP), application specific integrated circuit (ASIC), or some other digital processor with associated software. The processing circuitry 608 is adapted to compare the measured spectrum to characteristic frequencies associated with the molecular species of interest. The processing circuitry 608 can also send a control signal to a vehicle's engine if the molecular species of interest concentration is greater than a predetermined threshold.

Figure 7:
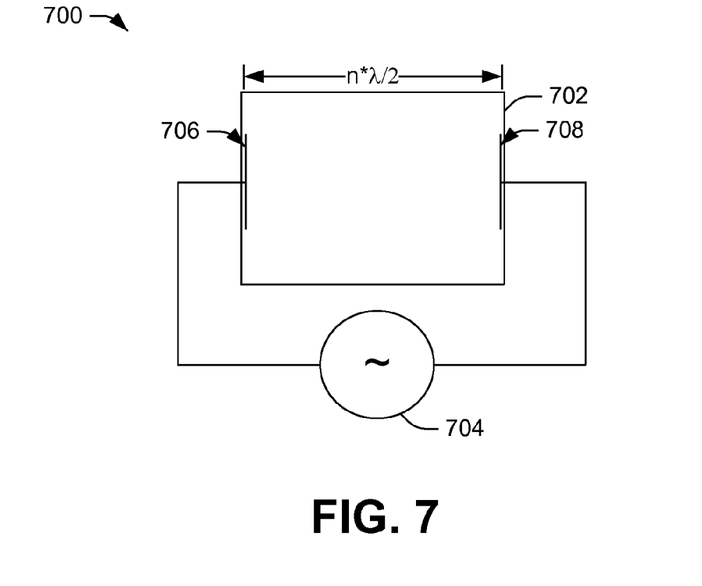
FIG. 7 shows an embodiment where a volume of gas is enclosed by a cavity resonator in accordance with an embodiment of the present invention.

FIG. 7 depicts another embodiment of a gaseous monitoring system 700 that includes a cavity resonator 702 for housing the volume of gas 104. The cavity resonator 702 is structured so its dimensions are an integer multiple of half the wavelength (i.e., $n*\lambda/2$) of the transmitted radiation. An oscillator 704 then facilitates generation of radiation between two electrodes 706, 708 that act as a transmitter and receiver. If a molecular species of interest is present in the volume of gas in the cavity resonator 702, the oscillation amplitude in the resonator 702 will vary in a manner that allows the molecular species of interest to be suitably identified.

Figure 8:
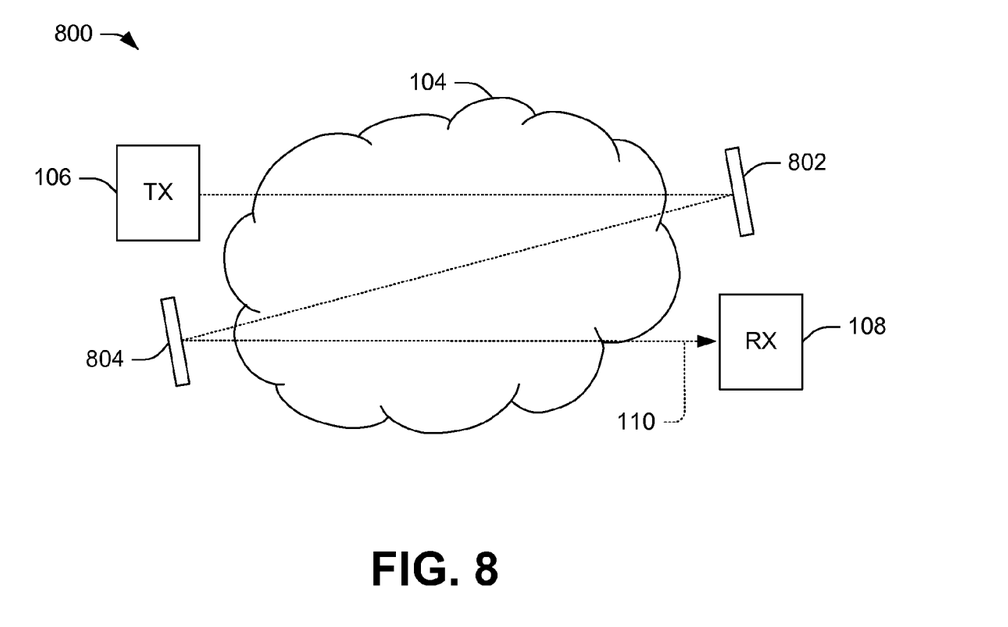
FIG. 8 shows an embodiment where two reflective surfaces are arranged about the outer perimeter of the volume of gas in accordance with an embodiment of the present invention.

FIG. 8 depicts another embodiment of a gaseous monitoring system 800 where a series of reflective surfaces 802, 804 are provided near the periphery of the volume of gas 104 to be analyzed. The reflective surfaces 802, 804 are arranged to cooperatively reflect the transmitted radiation through the volume of gas multiple times, thereby increasing the effective length of the transmission path 110 and enhancing the measuring effect. This embodiment is particularly advantageous in embodiments where the system 800 is small and the amount of gas molecules low. By lengthening the transmission path, the reflective surfaces 802, 804 increase the sensitivity and allow for more accurate measurement of the effect of molecules. In some embodiments, the reflective surfaces 802, 804 are made of metals such as Cu, but could also be made of other materials.

Figure 9:
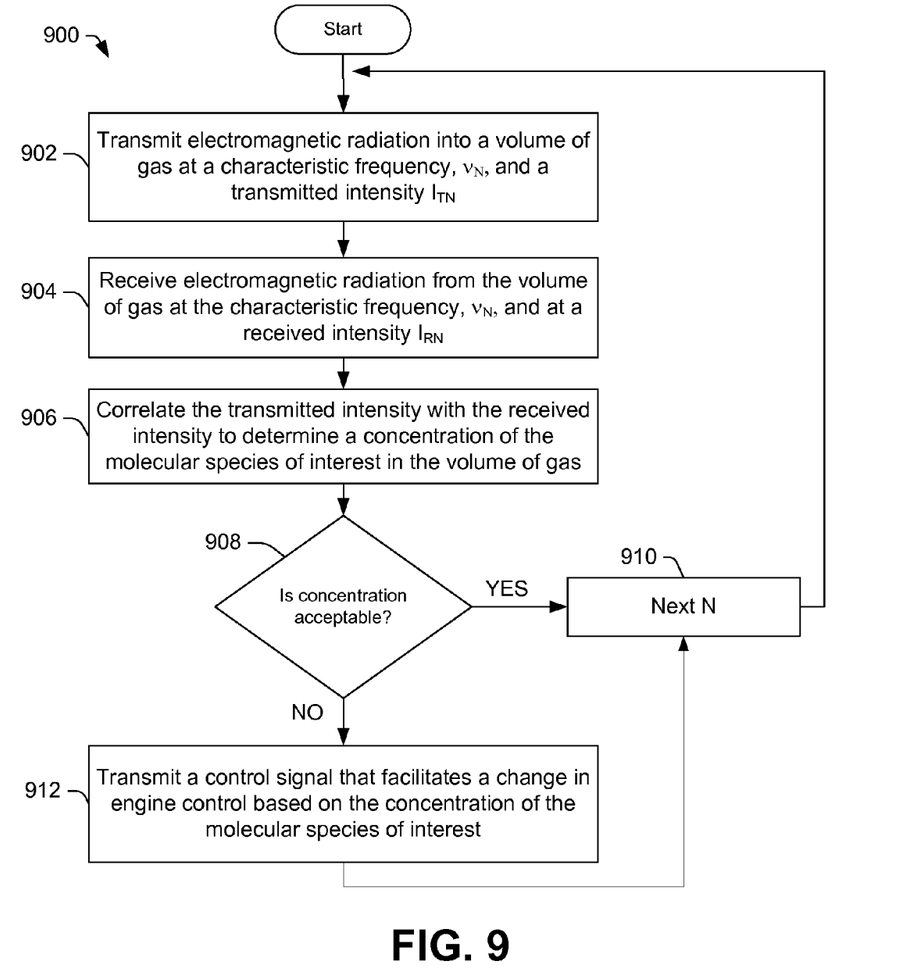
FIG. 9 is a flowchart illustrating an embodiment of a method for detecting the concentration of a molecular species of interest within a volume of gas by taking an absorption measurement.
Figure 10:
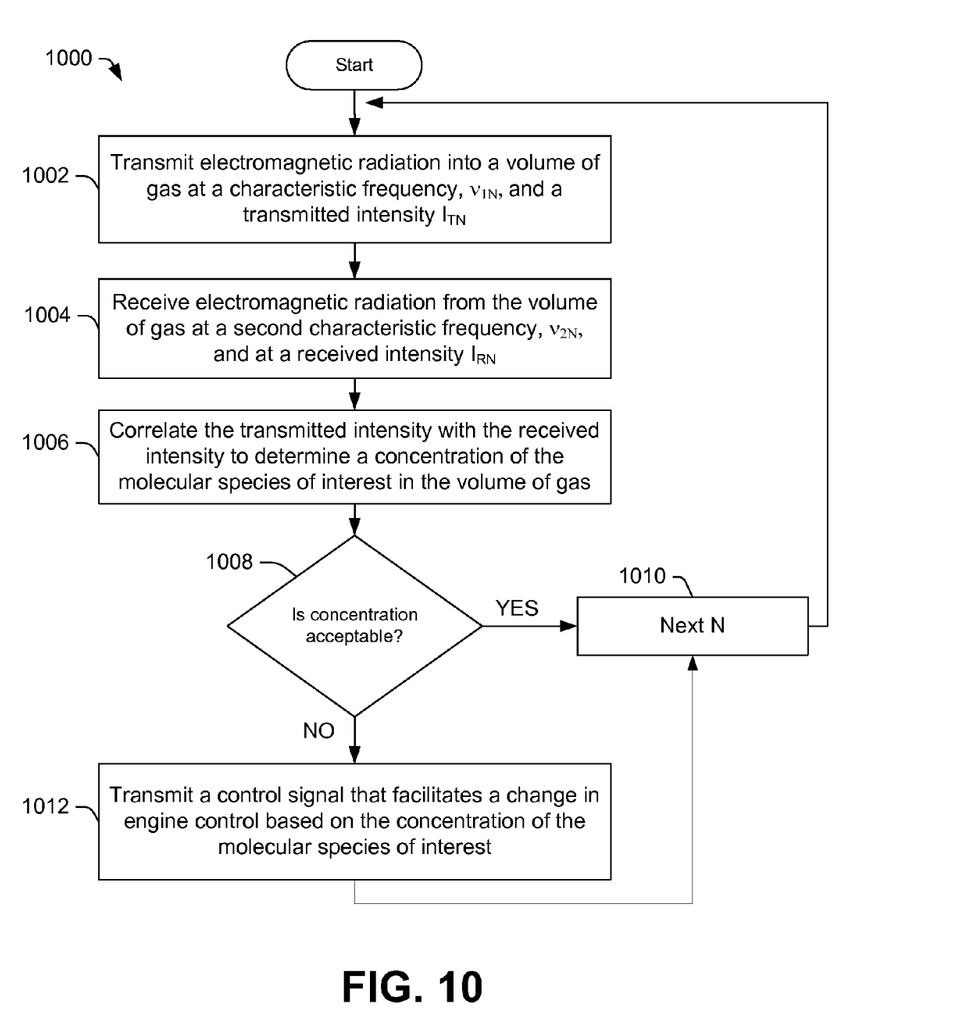
FIG. 10 is a flowchart illustrating an embodiment of a method for detecting the concentration of a molecular species of interest within a volume of gas by taking an emission measurement.

Now that some systems in accordance with aspects of the invention have been discussed, reference is made to FIGS. 9-10, which show methods in accordance with aspects of the invention. More particularly, FIG. 9 shows an example of a method for performing an absorption measurement and FIG. 10 shows an example method for performing an emission measurement. While these methods are illustrated and described below as a series of acts or events, the present invention is not limited by the illustrated ordering of such acts or events. For example, some acts may occur in different orders and/or concurrently with other acts or events apart from those illustrated and/or described herein. In addition, not all illustrated steps may be required to implement a methodology in accordance with one or more aspects of the present invention. Further, one or more of the acts depicted herein may be carried out in one or more separate acts or phases.

Referring to FIG. 9, electromagnetic radiation is transmitted into a volume of gas at block 902. The electromagnetic radiation is transmitted at a characteristic frequency $v_N$ and at a transmitted intensity $I_{TN}$.

In block 904, electromagnetic radiation is received at a received intensity $I_{RN}$ at the characteristic frequency $v_N$. This measurement is taken after the electromagnetic radiation has passed through a volume of gas that may contain the molecular species of interest. The extent to which the received intensity differs from the transmitted intensity depends on the concentration of the molecular species of interest in the volume of gas.

In block 906, the first intensity is correlated with the second intensity to determine a concentration of the molecular species of interest in the volume of gas.

In block 908, it is determined if the concentration is acceptable. If it is ("YES" at 908), the method 900 proceeds to 910 where the transmitter and receiver prepare to test another characteristic frequency. The method then continues the monitoring process as shown in an on-going manner.

If the concentration of the molecular species of interest is unacceptable ("NO" at 908), the method proceeds to block 912 and transmits a control signal. The control signal facilitates a change in engine control based on the concentration of the molecular species of interest. In this way, pollutants in exhaust can be reduced and vehicle performance can be improved. After the control signal is transmitted, the method proceeds to 910 where the transmitter and receiver prepare to test another characteristic frequency.

FIG. 10 shows a method 1000 for taking an emission measurement. In this method, radiation is transmitted at a first characteristic frequency $v_{IN}$ at 1002. Then in 1004, electromagnetic radiation caused by atomic emission is received at a second frequency, $v_{2N}$, which may differ from the transmitted frequency (and is typically less than the first characteristic frequency, $v_{1N}$).

Some methods and corresponding features of the present disclosure can be performed by hardware modules, software routines, or a combination of hardware and software. To the extent that software is employed, for example by a baseband processor or other processor associated with the radar system, the software may be provided via a "computer readable medium", which includes any medium that participates in providing instructions to the processor. Such a computer readable medium may take numerous forms, including but not limited to, non-volatile media, volatile media, and transmission media. Non-volatile media includes, for example, optical disks (such as CDs, DVDs, etc.) or magnetic disks (such as floppy disks, tapes, etc.). Volatile media includes dynamic memory, such as ferroelectric memory, SRAM, or DRAM. Transmission media includes coaxial cables, copper wire, fiber optics, etc. that could deliver the instructions over a network or between communication devices. Transmission media can also include electromagnetic waves, such as a voltage wave, light wave, or radio wave.

Although the invention has been illustrated and described with respect to one or more implementations, alterations and/or modifications may be made to the illustrated examples without departing from the spirit and scope of the appended claims. In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "including", "includes", "having", "has", "with", or variants thereof are used in either the detailed description and the claims, such terms are intended to be inclusive in a manner similar to the term "comprising".

What is claimed is:

1. A method for determining a concentration of a molecular species of interest, comprising:
   transmitting electromagnetic radiation into a volume of gas within an output exhaust system using a radiation transmitter, where the transmitted electromagnetic radiation has a first intensity at a characteristic frequency that is associated with a transition of the molecular species of interest;
   receiving electromagnetic radiation from the volume of gas that passes through the volume of gas along a transmission path at a second intensity, at a radiation receiver located at an end of the transmission path, wherein the transmission path corresponds to a path of the radiation if no interference occurs between the radiation and the molecular species of interest in the volume of gas; and
   correlating the first intensity to the second intensity using a controller to determine the concentration of the molecular species of interest within the volume of gas.

2. The method of claim 1, where the molecular species of interest comprise at least one of: nitrous oxide ($NO_x$) molecules or ammonia molecules.

3. The method of claim 1, further comprising:
   reflecting the transmitted electromagnetic radiation multiple times through the volume of gas using one or more radiation reflectors to enhance a difference between the first intensity and the second intensity.

4. The method of claim 1, further comprising:
   transmitting a control signal that facilitates a change in engine control based on the concentration of the molecular species of interest.

5. A method for determining a concentration of a molecular species of interest, comprising:
   transmitting electromagnetic radiation into a volume of gas along a transmission path using a radiation transmission source;
   receiving electromagnetic radiation from the volume of gas at a radiation receiver located at the end of the transmission path, wherein the transmission path corresponds to a path of the radiation if no interference occurs between the radiation and the molecular species of interest in the volume of gas; and
   correlating the transmitted electromagnetic radiation to the received electromagnetic radiation using a controller to determine the concentration of the molecular species of interest within the volume of gas.

6. The method of claim 5, where the molecular species of interest comprises at least one of: nitrous oxide ($NO_x$) molecules or ammonia molecules.

7. The method of claim 5, where a receive frequency at which the electromagnetic radiation is received is adjusted in time.

8. The method of claim 5, where a transmit frequency at which the electromagnetic radiation is transmitted is adjusted in time.

9. The method of claim 8, where a receive frequency at which the electromagnetic radiation is received is synchronously adjusted in time with the transmit frequency.

10. The method of claim 8, where a receive frequency at which the electromagnetic radiation is received is adjusted in time independent of the transmit frequency.

11. A gaseous monitoring system, comprising:
    a frequency-tunable transmitter adapted to transmit electromagnetic radiation through a volume of gas along a transmission path that includes a molecular species of interest, where the electromagnetic radiation has a first intensity at a characteristic frequency associated with the molecular species of interest; and
    a frequency-tunable receiver adapted to generate a time-varying voltage or current based on a second intensity at which the transmitted electromagnetic radiation is received through the volume of gas at the receiver located at the end of the transmission path, wherein the transmission path corresponds to a path of the radiation if no interference occurs between the radiation and the molecular species of interest in the volume of gas.

12. The system of claim 11, where the transmitter comprises:
    a transmit antenna;
    transmission semiconductor circuitry coupled to the transmit antenna; and
    frequency tuning circuitry adapted to adjust a frequency at which the electromagnetic radiation is transmitted.

13. The system of claim 11, where the receiver comprises:
    a receive antenna;
    reception semiconductor circuitry coupled to the receive antenna; and
    frequency tuning circuitry adapted to adjust a frequency at which the electromagnetic radiation is received.

14. A gaseous monitoring system, comprising:
    a frequency-tunable transmitter, comprising:
      a transmit antenna;
      transmission semiconductor circuitry coupled to the transmit antenna and adapted to facilitate transmission of electromagnetic radiation along a transmission path at a first intensity at a characteristic frequency associated with a molecular species of interest; and frequency tuning circuitry adapted to adjust a frequency at which the electromagnetic radiation is transmitted; and a receiver, comprising:

a receive antenna separated from the transmit antenna by a volume of gas located at an end of the transmission path, wherein the transmission path corresponds to a path of the radiation if no interference occurs between the radiation and the molecular species of interest in the volume of gas; and reception semiconductor circuitry coupled to the receive antenna and adapted to generate a time-varying voltage or current based on a second intensity with which the transmitted electromagnetic radiation is received at the receive antenna in time.

15. The system of claim 14, where the receiver further comprises:

processing circuitry adapted to correlate the first intensity to the second intensity to detect a concentration of the molecular species of interest in the volume of gas.

16. The system of claim 15, further comprising:

a cavity resonator in which the volume of gas resides.

17. The system of claim 15, further comprising:

at least two reflective surfaces arranged about a periphery of the volume of gas and cooperatively adapted to reflect the transmitted electromagnetic radiation through the volume of gas multiple times before the electromagnetic radiation reaches the receive antenna.

18. The system of claim 14, where at least one of the transmission semiconductor circuitry and reception semiconductor circuitry is adapted to operate at a frequency that falls within a frequency range of about 1 GHz to about 10 THz.

19. A gaseous monitoring system, comprising:

transmitting means for transmitting electromagnetic radiation along a transmission path at a first intensity and at a characteristic frequency associated with a molecular species of interest; and receiving means for generating a time-varying voltage based on a second intensity at which the transmitted electromagnetic radiation is received in time at an end of the transmission path, wherein the transmission path corresponds to a path of the radiation if no interference occurs between the radiation and the molecular species of interest in the volume of gas;

and processing means for correlating the first intensity to the second intensity to determine the concentration of the molecular species of interest in the volume of gas.

* * * * *